(12) United States Patent
Edlund et al.

(10) Patent No.: US 8,917,181 B2
(45) Date of Patent: *Dec. 23, 2014

(54) METHOD FOR MONITORING AN INDIVIDUAL

(71) Applicants: Mikael Edlund, Sodertalje (SE); Fredrik Bjorklund, Tyreso (SE)

(72) Inventors: Mikael Edlund, Sodertalje (SE); Fredrik Bjorklund, Tyreso (SE)

( * ) Notice: Subject to any disclaimer, the term of this patent is extended or adjusted under 35 U.S.C. 154(b) by 0 days.

This patent is subject to a terminal disclaimer.

(21) Appl. No.: 14/017,627

(22) Filed: Sep. 4, 2013

(65) Prior Publication Data

US 2014/0118148 A1    May 1, 2014

Related U.S. Application Data

(63) Continuation of application No. 13/695,072, filed as application No. PCT/US2011/030300 on Mar. 29, 2011, now Pat. No. 8,558,703.

(60) Provisional application No. 61/332,213, filed on May 7, 2010.

(51) Int. Cl.
   *G08B 23/00* (2006.01)
   *G08B 21/24* (2006.01)
   *G08B 21/04* (2006.01)

(52) U.S. Cl.
   CPC ............ *G08B 21/24* (2013.01); *G08B 21/0423* (2013.01); *G08B 21/0484* (2013.01)
   USPC ..................... 340/573.1; 340/506; 340/539.1; 455/456.3; 725/12; 725/133

(58) Field of Classification Search
   CPC ............... G08B 21/24; G08B 21/0484; G08B 21/0423; A01B 12/006
   USPC ................. 340/539.1, 506, 573.1; 455/456.3; 725/12, 133
   See application file for complete search history.

(56) References Cited

U.S. PATENT DOCUMENTS

| | | | |
|---|---|---|---|
| 2004/0060059 A1* | 3/2004 | Cohen | 725/30 |
| 2004/0117632 A1* | 6/2004 | Arling et al. | 713/182 |
| 2005/0240959 A1* | 10/2005 | Kuhn et al. | 725/25 |
| 2005/0286686 A1* | 12/2005 | Krstulich | 379/32.01 |
| 2007/0152837 A1* | 7/2007 | Bischoff et al. | 340/573.1 |
| 2008/0297363 A1* | 12/2008 | Fukushige | 340/635 |
| 2009/0287838 A1* | 11/2009 | Keyghobad et al. | 709/230 |
| 2011/0080291 A1* | 4/2011 | Ishimoto | 340/573.1 |
| 2011/0093876 A1* | 4/2011 | Belz et al. | 725/12 |
| 2011/0251807 A1* | 10/2011 | Rada et al. | 702/61 |
| 2012/0056746 A1* | 3/2012 | Kaigler et al. | 340/573.1 |
| 2012/0086573 A1* | 4/2012 | Bischoff et al. | 340/573.1 |
| 2013/0241727 A1* | 9/2013 | Coulombe | 340/517 |

* cited by examiner

*Primary Examiner* — Hai Phan
*Assistant Examiner* — Ojiako Nwugo
(74) *Attorney, Agent, or Firm* — Fasth Law Offices; Rolf Fasth

(57) ABSTRACT

An individual is monitored by providing a monitoring system having a control device in communication with appliances. A routine usage of the appliance by an individual is determined. A deviation from the routine usage of the appliance is detected. An alarm signal is sent to a remote communication device of a third party. The third party remotely manipulates the appliance via the control device to remove the deviation from the routine usage, such as turning off an iron or closing a refrigerator door, without involving the individual.

10 Claims, 2 Drawing Sheets

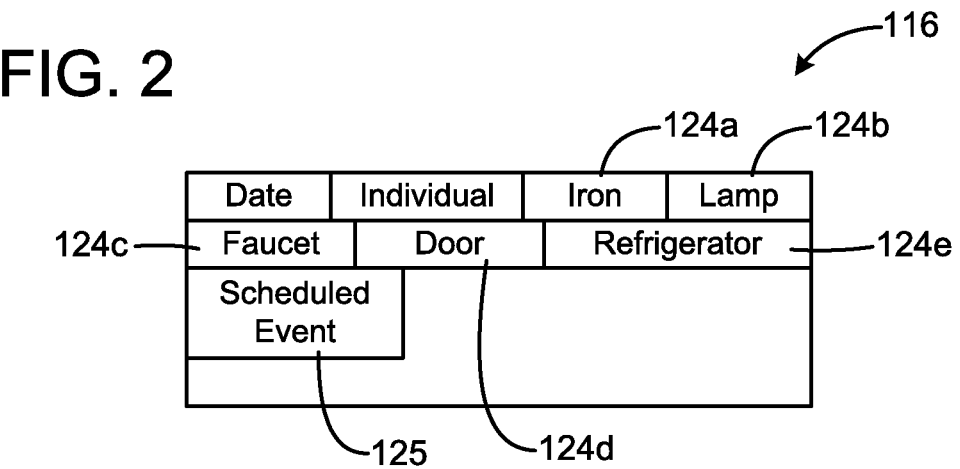
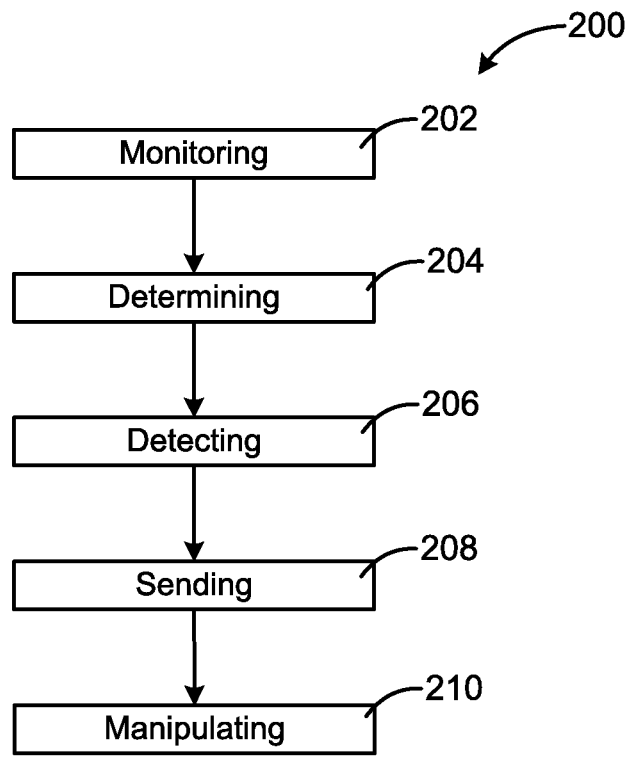

METHOD FOR MONITORING AN INDIVIDUAL

PRIOR APPLICATIONS

This is a continuation patent application that claims priority from U.S. patent application Ser. No. 13/695,072, filed 29 Oct. 2012, that claims priority from International Patent Application No. PCT/US11/030300, filed 29 Mar. 2011 and U.S. provisional patent application Ser. No. 61/332,213, filed 7 May 2010.

TECHNICAL FIELD

The invention relates to a method for monitoring an individual's behavioral pattern such as use of appliances in a home and also to detect deviations from normal behavior. Deviations could result in alarms, alerts and automatic measures as well as trigger actions taken by third party.

BACKGROUND OF INVENTION

There are many electrical and electronic devices in the modern household some of which can become dangerous if the user, for example, forgets to turn off one of the devices, such as an iron, or forgets to close the refrigerator door. There is a need for a reliable and effective way to monitor and assist individuals who are prone to forget to turn off such devices or otherwise cannot handle the devices in a safe manner.

SUMMARY OF INVENTION

The method of the present invention provides a solution to the above-outlined problems. More particularly, the method is for monitoring an individual by providing a monitoring system that has a control device in communication with appliances in the home of the individual. A routine usage of the appliance by the individual is determined. A deviation from the routine usage of the appliance is detected. An alarm signal is sent to a remote communication device of a third party. The third party remotely manipulates the appliance via the control device to remove the deviation from the routine usage, such as turning off an iron or closing a refrigerator door, without necessarily involving the individual. Measures to be taken could also be automatically triggered depending on the actual deviation. This may be handled by the server according to actual configuration in connection with certain events. The server may be an event-driven application that could handle and unlimited set of events and inter-connected events.

BRIEF DESCRIPTION OF DRAWINGS

FIG. 2 is a schematic view of an interface of the monitoring system of the present invention; and FIG. 3 is an information flow of the operation of the monitoring system of the present invention.

DETAILED DESCRIPTION

Figure 1:
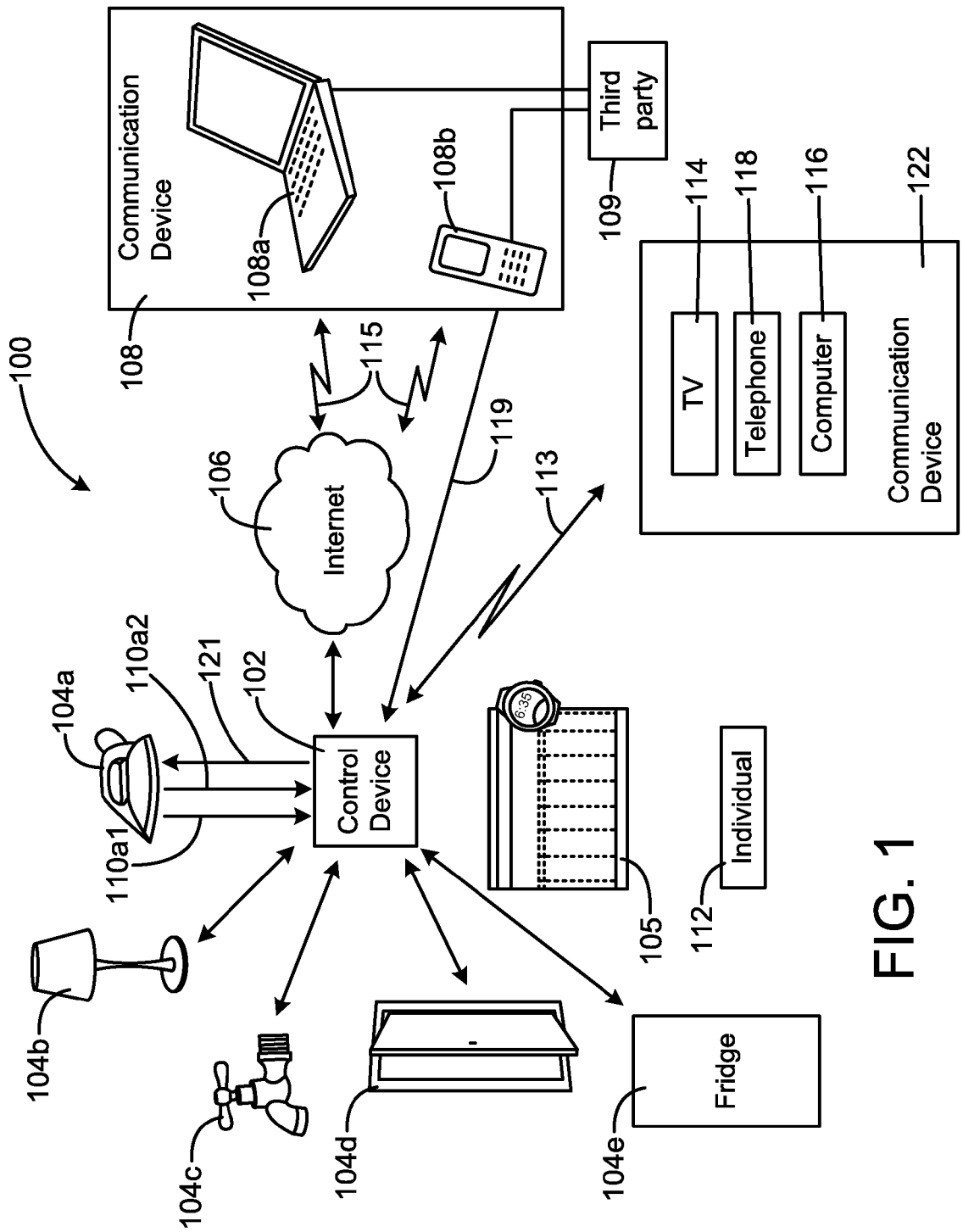
FIG. 1 is a schematic view of the monitoring system of the present invention.

In general, the method of the present invention relates to a fully integrated real-time monitoring system to assist an individual in his/her everyday living in a home. The individual, a care-giver and/or relative may all be connected to the system but have different interfaces if or when an alarm is triggered by a monitoring device, as explained in detail below. An important aspect of the present invention is that the system 100 may be customized to the specific needs of the individual and it is therefore important to determine the actual needs and the normal behavior of the individual during a regular day when customizing the design of the system 100. Particularly if the individual is suffering from dementia, has a cognitive deficiency, has had a stroke, is handicapped or otherwise is in need of special assistance. The system may also be used by normal individuals who do not need any special assistance.

With reference to FIG. 1, the monitoring system 100 of the present invention has a monitoring or control device 102 that, preferably, is communication with, such as by linking or being connected to, appliances 104 such as an iron 104a, lamp 104b, faucet 104c, motorized door 104d and refrigerator 104e. The control device 102 may be in communication with any number of appliances or devices as desired. The control device 102 may also be linked to a calendar feature 105 where future events may be scheduled and reminders be sent to the individual 112 such as when to take medicine. The successful taking of the medicine may be verified by the individual when it has been done. Other suitable appliances and electrical/electronic devices may also be linked to the control device 102, as desired.

The device 102 may via a network 106, such as the Internet, be linked to remote communication devices 108 such as a computer 108a and telephone 108b that is operated by a third party 109 or a plurality of third parties. It is possible to use a plurality of third parties that are ranked so that if an alarm signal goes to the first third party who does not respond within a very limited time period, then the alarm signal is sent to a second third party etc. until a proper and timely response is received. The third party 109 can be anybody selected to assist the individual 112 such as a care-giver, medical personnel, emergency unit or relative. An important feature of the monitoring system 100 of the present invention is that the appliances, via the control device 102, may be controlled and manipulated by the communication devices 108 as described in detail below.

Preferably, the control device 102 is linked to the appliances 104 in such a way that when one of the appliances 104 such as the iron 104a is turned on the control device 102 may sense this such as by receiving an on-signal 110a1 sensed by or sent to the control device 102 and when the iron 104a is turned off an off-signal 110a2 may be sensed by or sent to the control device 102. This communication may be done by wireless or wired technology. The status of all the other appliances 104 are sensed by the control device 102 in a similar manner. An important feature is that the control device 102 may measure or determine the length of the time period each appliance has been turned on or off. The control device 102 may also measure or determine other parameters such as when the appliance was turned on or off and, in the case of for example the iron 104a, the temperature of the heating element of the iron 104a.

When setting up or customizing the system 100 to needs of the individual 112, it is, for example, determined the maximum allowed time the iron 104a can be turned on without triggering a notification signal 113 or an alarm signal 115. This may be determined by how long the individual 112 usually needs to carry out a normal task with the iron, based on previous experience and data recording, and by what time period is a safe time period to prevent the iron 104a from causing damage such as a fire. In other words, it is possible to record the allowable time periods the various appliances can be turned on in the control device 102. Similarly, when it comes to doors or refrigerators, the system may, for example, determine the maximum amount of time the door 104*d* may be open without triggering the notification signal 113 and later the alarm signal 115.

Upon the triggering of the notification signal 113, the monitoring system 100 may not only verbally remind the individual 112 about the pending alarm situation, such as by broadcasting "Please turn off the iron," but also send reminder signals to a TV 114, computer 116, or different kinds of mobile devices of the individual 112 such as by showing a picture of an over-heating iron or a picture of the medicine that is due to be taken. It may even be possible for the system 100 to call a telephone 118 of the individual 112 so that the individual hears a voice instructing him to turn off the iron 104*a*. This could also be done through vibrations of the phone and different kinds of signals depending on the actual event.

If the appliance 104, such as the iron 104*a*, is not taken care within a time period such as turned off, despite the notification signal 113, the control device 102 sends out the alarm signal 115 to the third party 109. An important feature of the present invention is that upon receipt of the alarm signal 115 on one of the communication devices 108 such as the computer 108*a* or mobile telephone 108*b*, the third party 109 may in real time remotely turn off the iron 104*a*, turn off the light 104*b*, turn off the water 104*c*, close the motorized door 104*d* or manipulate any other appliance 104 associated with and controlled by the control device 102. These events could also be handled automatically according to the configuration of the server engine.

It is also possible to display the status in real time of the appliances 104, 105 in the household of the individual 112 as shown in the display 116 in FIG. 2. When the third party 109 sees that the individual 112 has forgotten something, such as turning off the iron 104*a* or closing the door 104*d*, the third party 109 may call the telephone 118 of the individual 112 to inform or remind the individual about him having forgotten to, for example, turn off the iron 104*a*. This may be displayed by a blinking light or by changing a color of a box 124*a* associated with the iron 104*a*. For example, a box may change the color from green when the status is acceptable to red when an alarm is triggered. The display 116 may also display other boxes 124*b*-124*e* associated with appliances 104*b*-104*e* or display the status of scheduled events 125 such as the taking of medicine or other events associated with calendar 105. The third party 109 may even offer to remotely turning off the iron 104*a* via the communication device 108 connected to the control device 102. A picture of the third party 109 and the over-heating iron 104*a* may also appear on a communication device 122 such as the TV 114, computer 116 or telephone 118. A manipulation signal 119 is then sent from, for example, the mobile telephone 108*b* to the control device 102 that in turn may verify the number of the mobile telephone 108*b* as being duly registered before sending a turning off signal 121 to the iron 104*a* that turns off the iron 104*a* without any involvement of the individual 112. Whether an alarm is triggered may also depend upon outside parameters such as when an outside temperature exceeds a certain temperature then, for example, the door 104*d* may be opened a longer period without triggering the notification signal 113 or alarm signal 115 compared to the time period allowed when the outside temperature is below the certain temperature.

It may also be possible for the control device 102 to turn off an appliance 104 directly without any involvement of a third party and the control device 102 may, after the fact, notify or send a message to the individual 112 and third party 109 about what action the control device 102 has already taken. It may also possible for the system 100 to turn on or turn off certain appliances or device at night or morning and to send out status signals on a regular basis to the third party 109. It may also be possible to display in real time on the display 116 that the individual 112 is, for example, using the iron 104*a* although there is no alarm situation yet in order to generally alert the third party 109. It is also possible to record the activities of how the individual 112 has used the appliances 104 during a day and present this in a log report. It may also be possible to monitor the energy consumption in the system and the third party may remotely reduce a temperature setting of, for example a radiator when needed. It may thus be possible to monitor and manipulate the actual energy consumption of each electrical item in the system 100 such as each electrical heating element. The system 100 may also measure passivity such as if the individual 112 is insufficiently active. If the individual is not using any appliances at all or the behavioral pattern is abnormal, an alarm signal may be triggered to the third party.

With reference to FIG. 3, the method of the present invention may be summarized in method steps 200. The individual 112 is monitored in a monitoring step 202 by providing the monitoring system 100 that has the control device 102 in communication with the appliances 104 in the household of the individual. A routine usage of the appliance by the individual 112 is determined in a determining step 204. A deviation from the routine usage of the appliance is detected in a deviation detecting step 206. This may mean that the individual is using, for example, the iron 104*a* longer than what was recorded when the routine usage was determined. It could also involve the detection of the individual not using enough appliances which may indicate that the individual has left the premises or is very sick. An alarm signal 115 is sent, in a sending step 208, to a remote communication device of a third party. The third party may then remotely manipulate the appliance 104, in a manipulating step 210, via the control device 102 to remove the deviation from the routine usage, such as turning off an iron or closing a refrigerator door, without involving the individual 112.

While the present invention has been described in accordance with preferred compositions and embodiments, it is to be understood that certain substitutions and alterations may be made thereto without departing from the spirit and scope of the following claims.

The invention claimed is:

1. A method for monitoring an individual, comprising: providing a monitoring system having a control device in communication with an appliance; determining a routine usage of the appliance by an the individual; prior to an alarm situation, alerting a third party that the individual is using the appliance by displaying, in real time, the individual's use of the appliance on a display, the control device detecting a deviation from the routine usage of the appliance; the monitoring system displaying a picture of the appliance on a communication device of the individual and sending an instruction to the individual to turn off the appliance, the individual failing to turn off the appliance within a time period, the control device automatically sending an alarm signal to a remote communication device of the third party; the third party remotely manipulating the appliance in real time by sending a manipulation signal from the remote communication device to the control device; and the control device receiving the manipulation signal and verifying an identifying number of the communication device as being registered before sending a turning off signal to the appliance to remove the deviation from the routine usage without involving the individual.

2. The method according to claim 1, wherein the method further comprises the third party turning off the appliance in real time from a mobile telephone.

3. The method according to claim 1, wherein the method further comprises sending a notification signal to the individual prior to sending the alarm signal to the third party.

4. The method according to claim 1, wherein the method further comprises the control device being in communication with the appliance to sense a status of the appliance.

5. The method according to claim 4, wherein the method further comprises the control device measuring a time period the appliance have been turned on.

6. The method according to claim 1, wherein the method further comprises determining a behavioral pattern of the individual's usage of the appliance to determine a maximum allowed time the appliances are permitted to be turned on.

7. The method according to claim 1, wherein the method further comprises sending the alarm signal only after a predetermined time after a notification signal has not affected a status of the appliance.

8. The method according to claim 7, wherein the method further comprises displaying the status of the appliance in a display.

9. The method according to claim 8, wherein the method further comprises displaying events associated with a calendar.

10. The method according to claim 1, wherein the method further comprises the control device turning off the appliance prior to sending an action signal to the third party and the individual.

* * * * *